(12) United States Patent
Llorach et al.

(10) Patent No.: US 6,746,428 B2
(45) Date of Patent: Jun. 8, 2004

(54) HIGH TEMPERATURE DRY HEAT STERILIZABLE SYRINGE BARREL AND NEEDLE CANNULA ASSEMBLY

(75) Inventors: Gerald Llorach, Edo de Mexico (MX); Catherine Felix-Faure, Grenoble (FR); Paul Nelles, Nazaire les Eymes (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 175 days.

(21) Appl. No.: 09/789,870

(22) Filed: Feb. 21, 2001

(65) Prior Publication Data

US 2002/0138042 A1 Sep. 26, 2002

(51) Int. Cl.[7] ................................. H61M 5/32
(52) U.S. Cl. ............... 604/199; 604/187; 604/264; 604/265; 604/272
(58) Field of Search .................. 604/199, 187, 604/192, 198, 272, 264, 265

(56) References Cited

U.S. PATENT DOCUMENTS

| | | |
|---|---|---|
| 3,278,357 A | 10/1966 | Gettig et al. |
| 3,430,627 A | 3/1969 | Kitaj |
| 4,240,423 A | 12/1980 | Akhavi |
| 4,468,223 A | 8/1984 | Minagawa et al. |
| 4,964,866 A | 10/1990 | Szwarc |
| 4,986,818 A | 1/1991 | Imbert et al. |
| 5,026,355 A | 6/1991 | Sweeney et al. |
| 5,282,792 A | 2/1994 | Imbert |
| 5,308,330 A | 5/1994 | Grimard |
| 5,338,309 A | 8/1994 | Imbert |
| 5,607,400 A | 3/1997 | Thibault et al. |
| 5,697,908 A | 12/1997 | Imbert et al. |
| 5,700,247 A | 12/1997 | Grimard et al. |
| 5,795,337 A | 8/1998 | Grimard |
| 6,004,296 A | 12/1999 | Jansen et al. |

Primary Examiner—Manuel Mendez
Assistant Examiner—Kathryn L Thompson
(74) Attorney, Agent, or Firm—David M. Fortunato

(57) ABSTRACT

A hypodermic syringe barrel and needle cannula assembly is provided that is capable of being dry heat sterilized at temperatures of greater than about 250° C. and up to about 350° C. in which the assembly includes a syringe barrel, a needle cannula and a bonding material, where the bonding material is stable above about 250° C., cures to provide a transparent bond, and affixes the needle cannula into the syringe barrel to provide the assembly with a post-sterilization needle pullout strength of at least about 30 newtons.

3 Claims, 3 Drawing Sheets

HIGH TEMPERATURE DRY HEAT STERILIZABLE SYRINGE BARREL AND NEEDLE CANNULA ASSEMBLY

FIELD OF THE INVENTION

The present invention is directed to a hypodermic syringe barrel and needle cannula assembly that is capable of being dry heat sterilized at high temperatures. The invention is more particularly directed to a hypodermic syringe barrel and needle cannula assembly that is capable of being dry heat sterilized at temperatures of greater than about 250° C. and up to about 350° C. in which the assembly comprises a syringe barrel, a needle cannula and a bonding material, where the bonding material fills a portion of the passageway into which the needle cannula is placed and thereby immobilizes and affixes the needle cannula to the tip of the syringe barrel. The selected bonding material is stable above about 250° C. and cures to provide a transparent bond. The amount of bonding material used is pre-selected, preferably in relation to the interference length of the passageway, to provide the assembly with post-sterilization needle pullout strength of at least about 30 newtons.

BACKGROUND OF THE INVENTION

Hypodermic syringes typically include an elongate cylindrical barrel having opposed proximal and distal ends and at least one chamber in between suitable for holding a substance such as a fluid medicament, drug or vaccine. The proximal end is open to allow the introduction of a plunger and may include a flange portion that functions as a finger hold. The distal end typically forms a tip that is closed except for a narrow passageway extending from the barrel chamber through the tip to the tip end and the exterior. A needle cannula is attached to the tip of the barrel directly within the passageway or indirectly via a needle holder. When the needle cannula is affixed into the passageway, it is typically attached with an adhesive.

Syringes with needle cannulas affixed with an adhesive are characterized by a dimension known as the "interference length" that defines that portion of the passageway measured from the tip end of the syringe barrel to the bottom end of the affixed-needle cannula. Prior art syringes are generally known to have an interference length of about 5 to 10 millimeters.

Dry heat sterilization at high temperatures is the preferred methodology for sterilizing glass and steel medical device products including syringes primarily due to its ability to destroy or inactivate microbial pyrogens and bacterial endotoxins that may have been left in the syringes during manufacture or processing. The preferred dry heat sterilization temperature is in the range of 250° C. to 350° C.

Prior art syringe barrel and needle cannula assemblies, however, could not survive temperatures approaching 250° C., primarily due to incineration and vaporization of the adhesives that were used to retain the needle cannulas in the syringe tips. The degradation processes of those adhesives have resulted in broken tips and/or loss of needle pullout strength. Additionally, at temperatures above about 180° C., most of the adhesives used in the assemblies exhibited coloration due to the heat, resulting in rejections based mainly on aesthetics. Until now, it has been necessary to sterilize hypodermic syringe barrel and needle cannula assemblies at substantially lower temperatures.

Accordingly, due to the incumbent advantages of high temperature dry heat sterilization, there has remained an on-going need to develop a hypodermic syringe barrel and needle assembly capable of being dry heat sterilized at temperatures of greater than about 250° C. without degradation to the adhesive used to affix the needle cannula to the syringe barrel.

SUMMARY OF THE INVENTION

The present invention is a hypodermic syringe barrel and needle cannula assembly capable of withstanding high temperature dry heat sterilization/-depyrogenation at temperatures of at least about 250° C. and up to about 350° C. As contemplated in the present invention, the needle cannula is affixed within the tip of the syringe barrel with a bonding material. The syringe barrel and needle cannula assembly (referred to herein as the "barrel assembly" or the "assembly") is capable of being dry heat sterilized at temperatures of at least about 250° C. and up to about 350° C. without any substantial degradation to the bonding material or the assembly. More specifically, the barrel assembly of the present invention preferably uses a polymer-based bonding material that includes a polymerization initiator and remains stable at temperatures greater than about 250° C. and up to about 350° C. The bonding material fills a portion of the crevice region that is formed between the exterior surface of the needle cannula and the interior surface of the passageway. The amount of bonding material used is pre-selected to provide the assembly with post-sterilization needle pullout strength of at least about 30 newtons or average needle pullout strength of at least about 60 newtons. The amount of bonding material used in the crevice region is characterized by a dimension referred to herein as the "bonding depth" that defines the depth of the adhesive in the passageway measured from the tip end. In the present invention, the bonding depth is preferably in relation to the interference length (as noted above, the "interference length" refers to the distance of the needle cannula within the passageway). While it is fully contemplated the bonding depth may vary with the outer dimension of the cannula, it is preferred that bonding depth be at least about 2 millimeters and up to about 100% of the interference length.

DETAILED DESCRIPTION OF A PREFERRED EMBODIMENT

Figure 1:
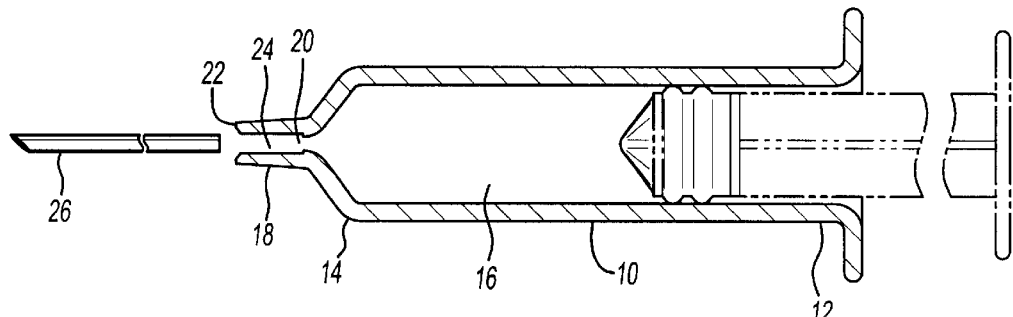
FIG. 1 shows a side-elevation cross-sectional view of an example of a hypodermic syringe barrel and needle cannula assembly in accordance with the present invention.
Figure 2:
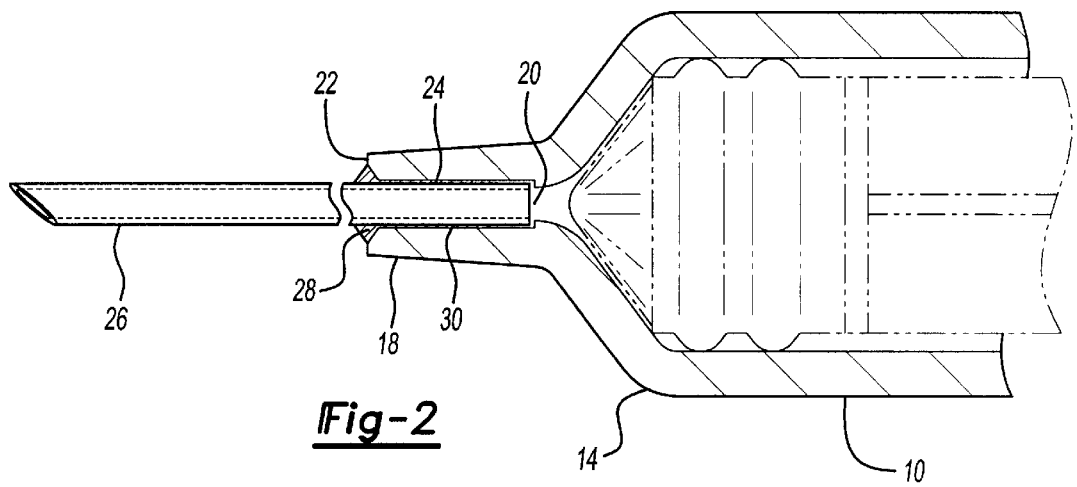
FIG. 2 shows an enlarged partial cross-sectional view of the syringe barrel and needle cannula assembly of FIG. 1 showing the crevice region between the needle cannula and the passageway.

A hypodermic syringe barrel and needle cannula assembly of the present invention is illustrated in FIGS. 1 and 2. The configuration shown is intended to be exemplary and not limiting in anyway. For example, syringe barrels contemplated for use in the present invention may have passageways of different configurations including, for example, ones that are tapered, ones with or without an interior ledge located near the bottom end of the passageway, ones in which the passageway is centered along the longitudinal axis of the barrel assembly, and ones in which the passageway is offset from the longitudinal axis of the assembly; and needle cannulas contemplated may be of any type including, for example, fine to thick gauge, short to long, and smooth to grooved. Accordingly, it will be recognized that a wide variety of syringe barrels and needle cannulas, while not shown, are contemplated and may be alternatively used in preparing assemblies of the present invention without departing from the intent of the invention.

Referring to FIG. 1, the barrel assembly of the present invention includes an elongate barrel 10 that has a proximal end 12 and a distal end 14 with at least one chamber 16 between the ends for receiving a substance such as a fluid medicament, drug or vaccine. Distal end 14 includes a tip 18 for holding a needle cannula 26. Tip 18 includes a passageway 24 having a bottom end 20 in communication with chamber 16 and a tip end 22 in communication with the exterior. When assembled as a completed syringe, proximal end 12 of barrel 10 is sealed with a plunger that is moveable within chamber 16.

Referring to FIG. 2, needle cannula 26 is affixed into tip 18 within passageway 24 with a bonding material 28 that fills at least a portion of the interference length of crevice region 30. Crevice region 30 defines the area between the outer surface of needle cannula 26 and the inner surface of passageway 24. Bonding material 28 fills the interference length of crevice region 30 to a pre-selected bonding depth sufficient to provide post-sterilization needle pullout strength of at least about 30 newtons. As contemplated, bonding material 28 preferably does not extend to the end of needle cannula 26 that is in communication with bottom end 20 in order to prevent possible clogging of needle cannula 26 by bonding material 28.

In assemblies of the present invention, while it is contemplated that the bonding depth may extend to the full length of passageway 24, it is preferred that the bonding depth be at least about 2 millimeters (mm) and up to about 100% of the interference length, in which the interference length is at least about 2 mm, and preferably about 6 mm to about 10 mm. In the barrel assembly of the present invention, while any suitable materials may be used, it is preferred that the needle cannula is made from stainless steel and the syringe barrel is made from glass.

The selected bonding material should be stable at temperatures above about 250° C., capable of being dried and/or cured rapidly to form a transparent bond, and suitable for bonding stainless steel to glass (or plastic). The selected bonding material should further be capable of being dried and/or cured using known energy sources such as, for example, heat, visible light, infrared energy, and/or ultraviolet energy. It will be recognized that any suitable energy source may be used that would be apparent to one of skill in the art including, for example, magnetic and/or electromagnetic flux, microwaves, x-rays, gamma rays, and the like.

The bonding material may be selected from any material or combination of materials that will meet the specified performance requirements including, for example, thermoplastics, polymer-based materials, epoxies, hot melt adhesives, heat-curable adhesives, UV (ultraviolet) curable adhesives, and combinations thereof. The bonding material preferably further includes an initiator suitable for promoting polymerization and/or curing of the selected bonding material. For example, the bonding material may be selected from a polyimide or other polymer-based material combined with a polymerization initiator or an UV-curable epoxy resin combined with an UV initiator.

As contemplated in the present invention, the inclusion of a suitable initiator in the bonding materials advantageously provides the ability to initiate "pre-curing", or partial curing, of the bonding material immediately upon, or subsequent to, needle cannula insertion into the syringe barrel while allowing the bonding material to fully cure over time. This is particularly advantageous when polymer-based or epoxy-based bonding materials are used. Upon activation of the initiator, such bonding materials will begin to increase in viscosity, or gel, thereby immobilizing the needle cannula within the passageway to facilitate later stage processing without process line interruption. Assemblies of the present invention may be so pre-cured because, prior to shipment and/or further processing, the assemblies are fully cured by suitable means including, for example, ultraviolet irradiation, heating or aging.

When the selected bonding material does not include an initiator, the needle cannula must be held in place until potting occurs. In such circumstances, the use of an instantly curing or fast curing bonding material is preferred.

One of the UV-curable epoxy adhesives preferred for use, as a bonding material in the present invention is glycidyl ether of bisphenol A epoxy adhesive. A commercially available adhesive that may be used as the bonding material, in the present invention, is Permabond DU176, distributed by the Permabond Division of National Starch & Chemical Company, Bridgewater, N.J.

It has been found that by using the bonding materials contemplated herein, especially UV curable epoxy adhesives, performance has improved by limiting tip breakage, needle pullout, and coloration at high temperatures. By the present invention, it has been found that such bonding materials, especially UV curable epoxy adhesives, may be advantageously used to securely affix the needle cannulas to the syringe barrels and provide the syringe barrel and needle cannula assemblies with the ability to undergo high temperature dry heat sterilization at temperatures above about 250° C.

It has been further found that bonding material performance in barrel assembly applications is directly related to the bonding depth. Optimal performance is obtained when the bonding depth extends sufficiently along the interference length of the crevice region to provide post-sterilization needle pullout strength of at least about 30 newtons. In the present invention it is preferred that the bonding depth be at least about 2 millimeters and up to about 100% of the interference length of the crevice region, and more preferred that the bonding depth be between about 70% to 90% of the interference length. In a most preferred embodiment, the bonding depth is between about 80% to 85% of the interference length.

Figure 3A:
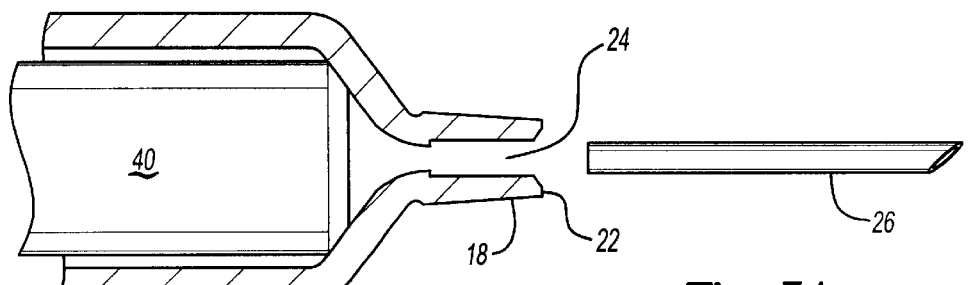
FIGS. 3A, 3B, 3C and 3D depict the incremental steps involved with the assembly of a syringe barrel and needle cannula assembly of the present invention.
Figure 3B:
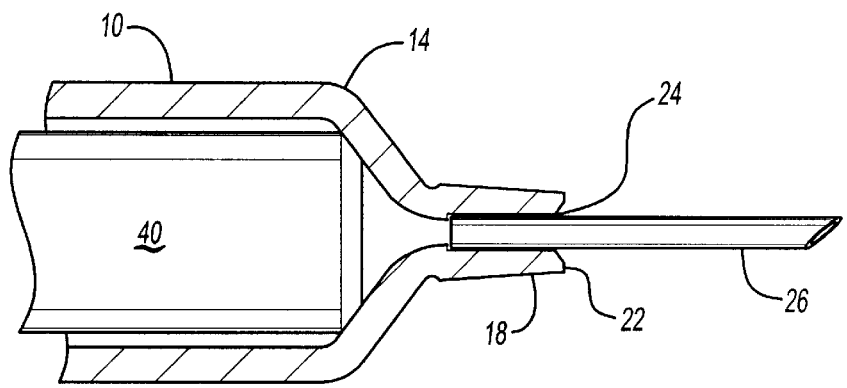
Figure 3C:
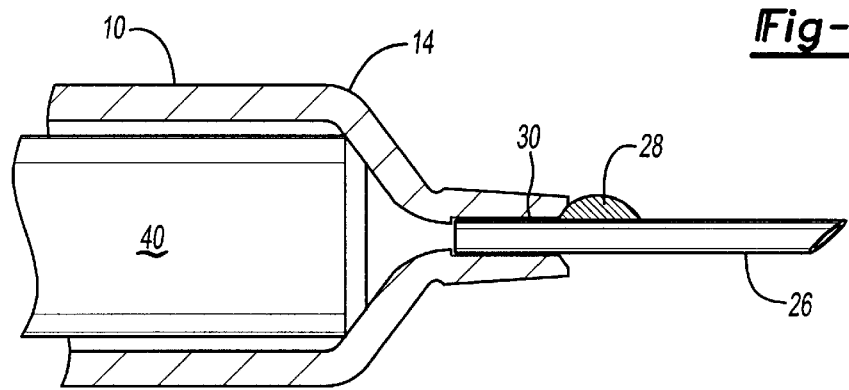
Figure 3D:
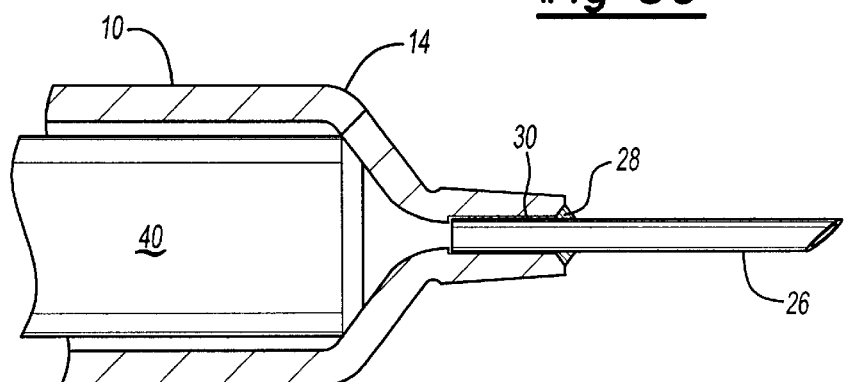

Syringe barrel and needle cannula assemblies of the present invention may be constructed using equipment known in the art. While assemblies of the present invention may also be constructed using any known methods, the methods described hereinafter are preferred. For example, in one process, a syringe barrel is extracted from a feeder and aligned on a rail. Referring to FIG. 3A, the proximal (open) end of each syringe barrel 10 is aligned with a rod 40 and gently settled onto it with the end of the rod extending through the inside to distal end 14 of syringe barrel 10. Referring to FIGS. 3A and 3B, the needle cannula 26 is taken from a second feeder, aligned with tip end 22 of tip 18 of syringe barrel 10 and gently inserted with its blunt end into passageway 24. Referring to FIG. 3B, passageway 24 is designed to accept needle cannula 26. Referring to FIG. 3C, a small pre-selected quantity of bonding material 28, sufficient to provide a post-sterilization needle pull-out strength of at least about 30 newtons, is placed drop-wise at the junction of tip 22 and needle cannula 26 and allowed to fill crevice region 30 by capillary action. The syringe barrel and needle cannula assembly prepared for curing is shown in FIG. 3D.

Figure 4A:
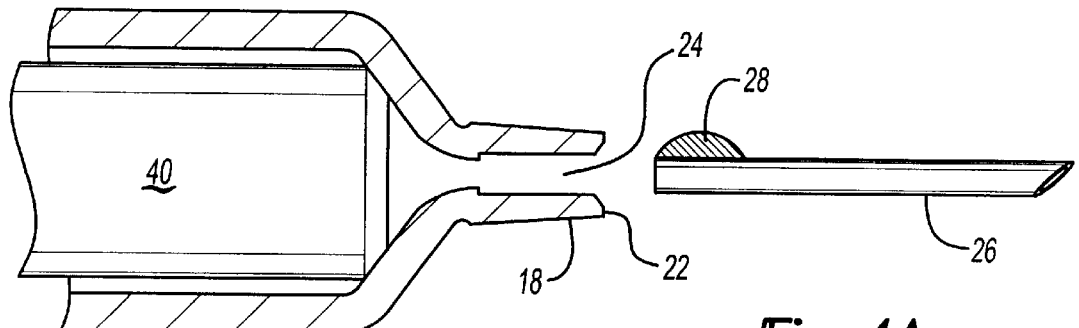
FIGS. 4A and 4B depict alternative process embodiments for applying the bonding material to a syringe barrel and needle cannula assembly of the present invention.
Figure 4B:
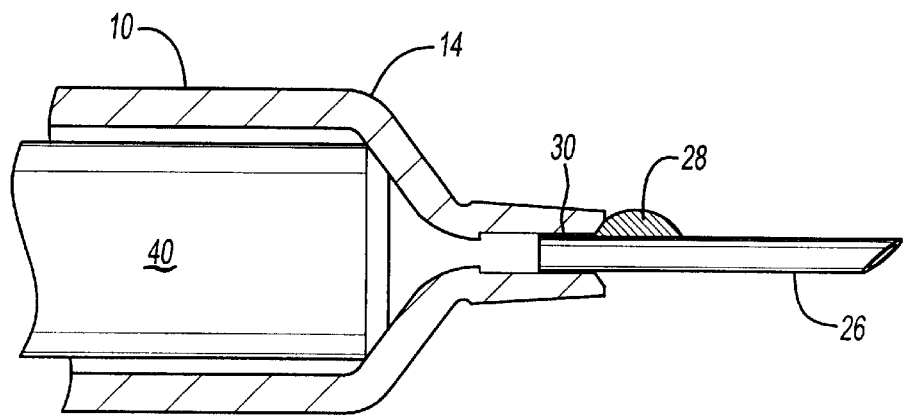

As shown in FIGS. 4A and 4B, the bonding material may be applied to the needle cannula in different ways. For example, referring to FIG. 4A, in one alternative embodiment, bonding material 28 may be placed onto needle cannula 26 prior to insertion into passageway 24. In another embodiment, as shown in FIG. 4B, bonding material 28 may be placed onto needle cannula 26 after it has been partially inserted into passageway 24, and then further inserted to its desired depth.

The bonding material in the syringe barrel and needle cannula assemblies may then be cured to create a transparent bond. The bonding material in the syringe barrel and needle cannula assembly is preferably pre-cured, followed by aging during which full cure is obtained. The syringe barrel and needle cannula assemblies are so aged for about 24 hours at room temperature or the equivalent, such as, for example, by accelerated aging for 2 hours at 100° C., or 5 minutes at 200° C. to 275° C., or the like, according to the bonding material characteristics and conditions of use.

Curing (or pre-curing) may be accomplished by any suitable means. For example, when an ultraviolet-epoxy adhesive bonding material is used, curing/pre-curing may be accomplished by UV irradiation at an absorption of between about 325 nm to about 375 nm, preferably between about 350 nm to about 375 nm, and more preferably about 365 nm, for up to about 25 seconds. Thermal curing may also be used for curing or final curing (following pre-cure) using, for example, a high intensity heat lamp at a temperature of between about 200° C. to about 275° C. for up to about 5 minutes.

Barrel assemblies of the present invention may be also be cured in combination with the sterilization process such that the bonding material is pre-cured and is fully cured during the initial stages of dry heat sterilization. For example, barrel assemblies of the present invention may be pre-cured and then followed by dry heat curing at about 250° C. to 300° C. for about 10 minutes. In addition, it is contemplated that full curing may be conducted solely during dry heat sterilization.

Barrel assemblies of the present invention may also be initially pre-cured and then fully cured after bulk packaging. For example, barrel assemblies intended for bulk delivery, as either bulk packaged or ready-to-use products, may be packaged immediately after assembly, followed by suitable curing methods such as, for example, thermal curing at low temperature or aging at room temperature. Barrel assemblies that are packaged for bulk delivery may be packaged according to any known system such as, for example, Rondo trays, bags or cartons.

Bulk packaged products may then be delivered, for example, to pharmaceutical industry users that process the barrel assemblies, fill them with a substance such as a fluid medicament, drug, vaccine, or the like, and package them for delivery to the end user. During such further processing, barrel assemblies of the present invention are unpacked from their packaging, distributed to a processing line, cleaned and/or washed, dried and sterilized.

Barrel assemblies of the present invention are preferably sterilized using dry heat following application of a suitable lubricant such as, for example, silicone oil that has been applied into the interior of the syringe barrel and onto the exterior of the needle cannula. Due to the ability of the present barrel assemblies to undergo dry heat sterilization, the lubricant can be applied pre-sterilization with the resulting advantage that the lubricant cures (or bakes) onto the assembly concurrent with the sterilization operation. Furthermore, the lubricant is cured (or baked) onto the assembly rather than individual components that must later be joined. In operation, silicone oil (or another lubricant) is preferably applied into the interior surface of the syringe barrel and onto the exterior surface of the needle cannula. The assembly is then dry heat sterilized during which process the silicone oil becomes cured (or baked) into the interior surface of the syringe barrel and onto the exterior surface of the needle cannula.

Following sterilization, a needle shield or similar needle protector is placed over the needle cannula. The substance such as a fluid medicament, drug, vaccine, or the like, is then filled into the barrel chamber, and a plunger stopper (which may include the plunger rod) is inserted into the barrel closing its open end. The assembly is then inspected and a plunger rod is added, if necessary, to complete syringe assembly. Complete filled syringes are then labeled and packaged for delivery to end-users.

Barrel assemblies of the present invention may also be packaged as ready-to-use products. As contemplated, such ready-to-use barrel assemblies may be further processed before or after bulk packaging. In either case, the bonding material is cured prior to the further processing and the bulk barrel assemblies are optionally aged. The bulk barrel assemblies are further processed by unpacking (if necessary) and distributing to a processing line. It will be recognized that such a processing line may be a separate line, or connected to, or a continuation of, the syringe barrel and needle cannula assembly line. The barrel assemblies are then cleaned and/or washed, dried and sterilized.

As described above, silicone oil (or a similar lubricant) is preferably applied into the interior of the syringe barrel and onto the exterior of the needle cannula prior to dry heat sterilization. The silicone oil is cured (or baked) to the assembly concurrent with dry heat sterilization. If necessary a separate heat treatment to cure the silicone oil may be used. Needle shields, or similar needle protectors, are then placed over the sterile needle cannulas. These sterilized assemblies may then be packaged in nests, trays, bags and/or cartons, and shipped to customers. Upon receipt, customers unpack the assemblies for direct filling with the intended substance. Following filling of the intended substance in the barrel chamber, a plunger stopper or the like (that may include a plunger rod) is affixed to the open end of the barrel chamber. Filled assemblies are inspected and plunger rods are attached (if necessary). The completed syringe assemblies may be labeled and packaged for shipment to syringe end-users.

Barrel assemblies of the present invention may be sterilized at any time after needle cannulas have been affixed to syringe barrels such as, for example, after needle cannula insertion, after partial adhesive cure, after full adhesive cure, after aging, or after delivery. As contemplated, syringe barrel and needle cannula assemblies of the present invention are intended to be capable of being sterilized/depyrogenated using commercially available dry heat sterilization/depyrogenation ovens and tunnels known in the art. Barrel assemblies of the present invention may be sterilized via batch or continuous processes using dry heat sterilization. As will be recognized by those of skill in the art, the temperatures and time periods selected for dry heat sterilization will be subject to governmental regulations and applicable pharmaceutical and/or pharmacological standards that exist in a particular local area. While such conditions may vary from one location to another, it is fully contemplated that the present assemblies will be capable of being dry heat sterilized under all such conditions. Without intending to be limiting in any way, it is contemplated that assemblies of the present invention may, for example, be dry heat sterilized at about 180° C. for about 3 hours, about 250° C. for about 45 minutes, about 300° C. for about 10 minutes, or about 350° C. for about 8 minutes.

The following example illustrates the performance of barrel assemblies made according to the present invention.

EXAMPLE

Assemblies according to the present invention were made using several UV-curing adhesives at various adhesive depths. All had stainless steel needles, glass syringe barrels, and an UV-curing adhesive. Results are shown for assemblies following curing and prior to sterilization, and then after dry heat sterilization at 300° C. for 10 minutes. Needle pullout tests were conducted on 30 samples of each test group (reported according to adhesive depth), while color and broken tips tests were conducted on 100 of each test group. A minimum post-sterilization average pullout force of 60 newtons was required for acceptance.

| Syringe Adhesive | Adhesive Depth | After UV Cure Pull Out Force (newtons) | | Color | Broken Tips | After 300° C. for 10 Minutes Pull Out Force (newtons) | |
|---|---|---|---|---|---|---|---|
| | | Avg. | Min | | | Avg. | Min |
| A | 80% | 116 | 58 | Clear | 6% | 139 | 46 |
| | 100% | 77 | 43 | Clear | 0% | 141 | 89 |
| B | 80% | 78 | 42 | Clear | 0% | 121 | 46 |
| | 100% | 75 | 40 | Clear | 4% | 141 | 44 |
| C | 80% | 78 | 42 | Clear | 2% | 145 | 63 |
| | 100% | 95 | 41 | Clear | 3% | 141 | 99 |
| D | 50% | 150 | 105 | Clear | 1% | 107 | 37 |
| | 100% | 116 | 51 | Clear | 2% | 85 | 35 |
| E | 50% | 119 | 67 | Clear | 0% | 109 | 36 |

As shown, all assemblies demonstrated substantially higher average post-sterilization pullout force than the threshold of 60 newtons; 0% broken tips were achievable; and color was consistently clear. In addition, all assemblies demonstrated minimum pullout force of at least 30 newtons.

While the preferred embodiment of the present invention has been described so as to enable one skilled in the art to practice the hypodermic syringe barrel and needle cannula assemblies of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed:

1. A dry heat sterilized hypodermic syringe barrel and needle cannula assembly comprising, an elongate barrel having a proximal end and a distal end with at least one chamber formed between the ends, said distal end culminating in a tip wherein said tip includes a bottom end in communication with the interior of said barrel and a tip end in communication with the exterior and a passageway in between said bottom end and said tip end for holding a needle cannula therein, a needle cannula affixed into said passageway with a bonding material that fills at least a portion of the interference length along said passageway to a bonding depth of at least about 2 millimeters and up to about 100% of said interference length, and a lubricant applied into the interior of said barrel and onto the exterior of said needle cannula prior to sterilization and heat cured into said interior of said barrel and onto said exterior of said needle cannula during dry heat sterilization, wherein said assembly is sterilized using dry heat at a temperature of at least about 250° C. and, following sterilization, said bonding material has no substantial coloration and said assembly has a needle pullout strength of at least about 30 newtons.

2. An assembly of claim 1 wherein said bonding material comprises an ultraviolet-curable epoxy adhesive and said lubricant comprises silicone oil.

3. An assembly of claim 1 wherein said temperature is about 300° C. and the average needle pullout strength is at least about 60 newtons.

* * * * *